US006296833B1

(12) United States Patent
Brown et al.

(10) Patent No.: US 6,296,833 B1
(45) Date of Patent: *Oct. 2, 2001

(54) HUMAN CALCIUM-SENSING RECEPTOR IN THE DETECTION AND TREATMENT OF CANCER

(75) Inventors: Edward M. Brown, Milton; David I. Soybel, Dover, both of MA (US)

(73) Assignee: The Brigham and Women's Hospital, Inc., Boston, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/238,495

(22) Filed: Jan. 27, 1999

Related U.S. Application Data

(60) Provisional application No. 60/073,222, filed on Jan. 30, 1998, and provisional application No. 60/082,259, filed on Apr. 17, 1998.

(51) Int. Cl.$^7$ ..................................................... A61K 49/00
(52) U.S. Cl. ........................ 424/9.1; 424/1.11; 424/1.49; 424/1.65; 424/130.1
(58) Field of Search ................................... 424/1.11, 9.1, 424/9.3, 9.4, 9.5, 9.6, 9.7, 9.8, 1.37, 1.49, 1.53, 1.61, 1.65, 1.69, 130.1; 514/183

(56) References Cited

U.S. PATENT DOCUMENTS

| 5,173,509 | 12/1992 | Walther et al. ...................... 514/597 |
| 5,277,894 | * 1/1994 | Strauss et al. ....................... 424/1.49 |
| 5,489,525 | * 2/1996 | Pastan ................................. 435/7.23 |
| 5,688,938 | 11/1997 | Brown et al. ........................ 536/23.5 |

FOREIGN PATENT DOCUMENTS

| 614 893 | 2/1994 | (EP) | ............................. C07D/265/36 |
| 2 670 785 | 12/1990 | (FR) | ............................. C07D/417/12 |
| 1033736 | 5/1963 | (GB) | ................................ A61K/3/00 |
| 1033737 | 8/1964 | (GB) | ................................ A61K/3/00 |
| WO 94/18959 | 9/1994 | (WO) | ............................. A61K/31/00 |
| WO 94/28019 | 12/1994 | (WO) | ............................. C07K/14/705 |
| WO 96/19226 | 6/1996 | (WO) | ............................. A61K/31/565 |
| WO 97/08201 | 3/1997 | (WO) | ............................. C07K/14/47 |
| WO 97/37967 | 10/1997 | (WO) | ............................. C07C/217/34 |
| WO 97/44050 | 11/1997 | (WO) | ............................. A61K/35/16 |

OTHER PUBLICATIONS

Farnebo, et al., "Differential Loss of Heterozygosity in Familial, Sporadic, and Uremic Hyperparathyroidism," *Hum. Genet.* 99:342–349 (1997).

International Search Report for PCT/US99/02062. (1999).

Dialog abstract of FR patent document No. 2 670 785 (listed above as document AP1), Derwent World Patents Index accession No. 92–278402/199234. (1990).

Dialog abstract of EP patent document No. 614 893 (listed below as document AM2), Derwent World Patents Index accession No. 94–334304/199442. (1994).

Dialog abstract of Larocca, et al., "Treatment of Cancer in Patient—By Administering Suramin Sodium at Levels to Produce Low Serum Concentrates to Avoid Neurotoxic Side Effects," U.S. Dept of Health & Human Services (1989).

Aida, et al., "Familial Hypocalciuric Hypercalcemia Associated with Mutation in the Human $Ca^2$–Sensing Receptor Gene," *J. Clin. Endocrinol. Metab.* 80 :2594–2598 (1995).

Aida, et al., "Molecular Cloning of a Putative $Ca^{2+}$–Sensing Receptor cDNA from Human Kidney," *Biochem. Biophys. Res. Commun.* 214:524–529 (1995).

Brown, et al., "Cloning and Charactertization of an Extracellular $Ca^2$–Sensing Receptor from Bovine Parathyroid," *Nature* 366:575–580 (1993).

Brown, et al., "Calcium Ions as Extracellular Messengers," *Cell* 83:679–682 (1995).

Pollak, et al., "Mutations in the Human $Ca^{2+}$–Sensing Receptor Gene Cause Familial Hypocalciuric Hypercalcemia and Neonatal Severe Hyperparathyroidism," *Cell* 75:1297–1303 (1993).

Pollak, et al., "Familial Hypocalciuric Hypercalcemia and Neonatal Severe Hyperparathyroidism: Effects of Mutant Gene Dosage on Phenotype," *J. Clin. Invest.* 93:1108–1112 (1994).

Pollak, et al., "Autosomal Dominant Hypocalcaemia Caused by a $Ca^2$–Sensing Receptor Gene Mutation," *Nature Genet.* 8:303–307 (1994).

Ruat, et al., "Calcium Sensing Receptor: Molecular Cloning in Rat and Localization to Nerve Terminals," *Proc. Natl. Acad. Sci. USA* 923161–3165 (1995).

* cited by examiner

Primary Examiner—Dameron L. Jones
(74) Attorney, Agent, or Firm—Michael A. Sanzo; Pillsbury Winthrop LLP

(57) ABSTRACT

The present invention is directed to methods for treating cancer patients by administering ligands that bind with specificity to the calcium-sensing receptor. In addition, the invention is directed to methods for detecting transformed cells by determining the number of calcium-sensing receptors present.

6 Claims, No Drawings

HUMAN CALCIUM-SENSING RECEPTOR IN THE DETECTION AND TREATMENT OF CANCER

CROSS REFERENCE TO RELATED APPLICATIONS

This application claims the benefit of U.S. Provisional Application No. 60/073,222, filed on Jan. 30, 1998 and also of U.S. Provisional Application No. 60/082,259, filed on Apr. 17, 1998.

STATEMENT OF GOVERNMENT SUPPORT

The work leading to this invention was supported by one or more grants from the U.S. Government. The U.S. Government therefore has certain rights in the invention.

FIELD OF THE INVENTION

The present invention is in the field of medical diagnostics and therapeutics. It is specifically directed to methods for detecting and treating cancer based upon the expression of the calcium-sensing receptor (CaR) in transformed tissue.

BACKGROUND OF THE INVENTION

An extracellular calcium-sensing receptor (CaR) has been cloned from both bovine and human parathyroids, as well as from human kidney tissue and rat brain (Pollak, et al., *Cell* 75:1297–1303 (1993); Aida, et al.,*Biochem. Biophys. Res. Commun.* 214:524–529 (1995); Ruat, et al., *Proc. Nat'l Acad. Sci. USA* 92:3161–3165 (1995)). This receptor appears to play a key role in regulating extracellular calcium homeostasis (Pollak, et al., *Nature Genet.* 8:303–307 (1994); Pollak, et al., *J. Clin. Invest.* 93:1108–1112 (1994)).

Previous studies have suggested that calcium may be important in processes leading to tumor formation and spread. For example, it is known that cancerous breast and brain tissue tends to form microcalcifications (Galkin, et al. *Radiology* 124:245–249 (1977)) and calcium has been shown to stimulate cellular division and differentiation. Defining the relationship between calcium and tumor cell biology may lead to new clinical approaches to treating cancer patients. The present invention is based upon the discovery that CaR, a primary regulator of calcium, is expressed at abnormal levels in human tumors. This has led to the development of new diagnostic and therapeutic methods.

SUMMARY OF THE INVENTION

The present invention is directed to a method for treating cancer in a human patient by administering a ligand that binds with specificity to CaR. Specific conditions that may be treated in this manner include breast cancer, prostate cancer, multiple myeloma, brain tumors, Leydig cell tumors, colon cancer, renal cell carcinoma, cervical cancer, ovarian cancer, vulvar cancer, skin cancer, esophageal cancer, lung cancer and cancers of the head or neck. For the purposes of the present invention, a ligand "binds with specificity" if it has at least a hundred-fold greater affinity for CaR than for any other protein. It is expected that some cancers will respond to calcium agonists whereas others will respond to calcium antagonists. The preferred calcium agonists are those agents described in PCT/US93/01642 and U.S. Pat. No. 5,688,938 (particularly the compound designated as NPS S-568). Other examples of calcium agonists that may be used include protamine and neomycin. An example of a calcium antagonist that may be administered to patients is suramin. However, other small molecular weight antagonists may be developed that will offer advantages over suramin and be preferred.

The calcium ligand should be administered at a dosage and for a duration sufficient to produce an improvement in one or more of the symptoms associated with the cancer being treated. Examples of such symptomatic improvement include a stabilization or reduction in tumor size or growth, a reduction in metastases, a normalization of calcium metabolism as reflected in parameters such as blood or tissue calcium concentrations, rate of bone resorption, etc. It has been discovered that CaR-specific ligands may be used to inhibit the production of parathyroid hormone related peptide (PTH-RP). Thus, antagonists may be given to a patient with cancer at a dosage sufficient to reduce plasma levels of PTH-RP and thereby reduce symptoms associated with aberrant calcium metabolism, particularly excessive bone resorption, or hypercalcemia.

The present invention is also directed to a method for detecting neoplastically transformed cells in a human patient by quantitating the number of CaR receptors present in test tissue, e.g. tissue obtained at biopsy, and comparing the results to those obtained from tissue known to be normal. The presence of transformed cells is indicated by a statistically significant increase or decrease in receptor number. One way to determine receptor number is by carrying out a binding assay using a detectably labeled ligand that binds with specificity to CaR. In a preferred embodiment, the ligand used in this method is a CaR-specific antibody. Biopsy tissue for use in the method includes tissue from the breast, prostate, brain, lung, cervix, ovary, colon or tissue comprised of Leydig cells. In the case of tissue from the colon, the presence of transformed cells is indicated by a lower number of CaR receptors compared to the number of CaR receptors in normal colon tissue.

In another aspect, the present invention is directed to a method for determining whether an abnormal growth, typically a tumor-like mass, in a human patient is cancerous. This is accomplished by administering a compound that binds with specificity to the calcium-sensing receptor and that is labeled with an agent that allows the compound to be detected using in vivo imaging techniques such as X-rays, sonograms, CAT scans, or magnetic resonance imaging. The extent to which the detectably labeled compound of step a) becomes localized in the abnormal growth is then determined and compared with the amount in tissue known to be noncancerous. If the amount of labeled compound in the abnormal growth is present at a statistically higher or lower level than the amount found in the nontransformed tissue, this is an indication that the abnormal growth is cancerous. It is expected that this method will be especially useful in determining whether a lump in a woman's breast is a cyst or a cancerous growth. The method may also be used to examine abnormal growths from the colon, lung, or brain.

In other work, it has been discovered that, when the calcium-sensing receptor is activated, cells become more resistant to apoptosis. This suggests two ways in which agents that interact with CaR may be used to augment the action of chemotherapeutic agents. In cases where a patient is treated with a chemotherapeutic agent that acts by inducing apoptosis in cancer cells, the method may be improved by the coadministration of a CaR antagonist. The antagonist should be administered at a dosage sufficient to sensitize the cancer cells, i.e. to induce a statistically significant higher percentage of the cells to undergo apoptosis in response to a fixed concentration of chemotherapeutic agent. Any method may be used to determine whether a given dosage of antagonist has caused apoptotic activity in cells to change. For example, cells may be stained and examined microscopically to determine the percentage with an apoptotic morphology (nuclear and cytoplasmic condensation, nuclear fragmentation, membrane blebbing, and apoptotic body formation). By performing such an assay both before and after the administration of CaR antagonist, one can determine if a statistically significant change has occurred.

In cases where a patient is treated with a chemotherapeutic agent that acts by some means other than inducing apoptosis in cancer cells but which induces apoptosis in normal cells as a side effect, the method may be improved by the coadministration of a CaR agonist. The agonist should be administered at a dosage effective to make cells more resistant to apoptosis. In this manner, the therapeutic efficacy of a treatment may be maintained while its undesirable side effects are decreased. In addition the invention includes the compositions that are used in the methods. Thus, it includes both compositions comprising a cancer chemotherapeutic agent and a CaR antagonist and compositions comprising a cancer chemotherapeutic agent and a CaR agonist.

The present invention encompasses not only a method for augmenting cancer chemotherapy as discussed above, but also, more generally, a method of altering the sensitivity of the cells of a mammal to apoptosis by administering an effective dose of a ligand that binds with specificity to the CaR receptor. Thus, CaR agonists and antagonists may be used in the treatment of diseases characterized by abnormal apoptotic activity, including autoimmune diseases and AIDS. The agents should be given at a dosage effective to cause an improvement in at least one symptom associated with the disease treated following the basic guidelines discussed in connection with cancer chemotherapy.

DETAILED DESCRIPTION OF THE INVENTION

Cancer patients, particularly patients with multiple myeloma or tumors of the breast, prostate, brain, colon, kidney, ovary, cervix, esophagus, skin or lung, may be treated by administering a ligand specific for CaR. Depending upon the particular cancer being treated, either antagonists or agonists of calcium may be effective. Thus, a physician should begin by administering a low dose of either an agonist such as protamine or neomycin, or an antagonist, such as suramin. A determination should then be made as to whether there is an improvement in one or more of the symptoms associated with the cancer. An improvement would be evidenced by a reduction in tumor growth, a reduction in tumor size, a reduction in the number of metastases associated with the tumor, improved calcium balance within the patient's blood, reduced bone absorption of calcium, or in an improvement in any other clinical parameter typically associated with cancer patients. If no response is seen at the initial dosage, it may be then raised until a maximum is reached. For example, a physician may begin by initially administering suramin at a dosage of 1 nmol/kg/day and increase the dosage up to a maximum of 1 $\mu$mol/kg/day. During this time, the symptoms of the patient would be periodically evaluated. If no improvement was observed over a period of, for example, three months, the patient may be switched to a calcium agonist and the procedure repeated. These are, of course, simply guidelines. Actual dosages will be carefully selected and titrated by the attending physician based upon clinical factors unique to each patient. The optimal daily dose will be determined by methods known in the art and will be influenced by factors such as the age of the patient, disease state, side effects associated with the particular agent being administered and other clinically relevant factors.

The present invention is not limited to any particular dosage form or route of administration. Although oral administration will generally be most convenient, the invention is compatible with parenteral, transdermal, sublingual, buccal, or implantable routes of administration as well. Agents may be given in a substantially purified form or, preferably, as part of a pharmaceutical composition containing one or more excipients or flavoring agents. The preparations may be solid or liquid and take any of the pharmaceutical forms presently used in medicine, e.g., tablets, gel capsules, granules, suppositories, transdermal compositions or injectable preparations. The active ingredient or ingredients may be incorporated into dosage forms in conjunction with the vehicles which are commonly employed in pharmaceutical preparations, e.g., talc, gum arabic, lactose, starch, magnesium stearate, cocoa butter, aqueous or non-aqueous solvents, oils, paraffin derivatives, glycols, etc. Methods for preparing appropriate formulations are well known in the art (see e.g. *Remington's Pharmaceutical Sciences*, 16th ed., A. Oslo ed., Easton, Pa. (1980)).

Compositions may also include other active ingredients for the treatment of patients. In particular, compositions may contain cancer chemotherapeutic agents such as cisplatin, tamoxifen, paclitaxel, vincristine and vinblastin. As mentioned above, it has been found that CaR activation makes cells more resistant to apoptosis. Therefore, if a chemotherapeutic agent acts by inducing apoptosis in cancer cells, the presence of a CaR antagonist may increase its effectiveness. Alternatively, if a chemotherapeutic agent exerts its therapeutic effect in some other way but, as a side effect, induces apoptosis in normal cells, the presence of a CaR agonist may reduce this side effect without adversely affecting efficacy.

In order to determine the effect of a treatment on disease, patients should be evaluated on a regular basis over an extended period of time. It may take several weeks for the full therapeutic effect of a treatment to become apparent. The effect of treatment on apoptotic activity can be determined on biological samples obtained from the patient by staining tissue samples and examining them microscopically to look for morphological characteristics indicative of programmed cell death. Blood may be assayed for calcium levels using standard procedures and levels of PTH-RP may be determined using methods described in the art. By comparing the results obtained to those obtained in samples from normal individuals, conclusions concerning the effectiveness of a treatment may be made. The effect of treatment on tumor size, tumor growth and tumor metastasis may be determined using standard radiological procedures.

In another aspect, the present invention is directed to a method for detecting transformed cells by quantitating the number of CaR receptors present in tissues suspected of being cancerous and comparing the results with those obtained from normal tissue. The presence of a statistically significant change in the number of receptors is indicative of transformation. One method for determining the number of receptors present is to incubate biopsy tissue with a detectably labeled ligand that binds with specificity to CaR. Typically, a CaR-specific antibody will be labeled with a radioactive isotope (e.g., $^{125}$I) or with an easily quantitatable enzyme, e.g. horseradish peroxidase. Methods for making appropriate antibodies are well known to those of skill in the art as evidenced by standard reference works such as: Harlow, et al., *Antibodies, A Laboratory Manual*, Cold Spring Harbor Laboratory, N.Y. (1988); Klein, *Immunology:*

*The Science of Self-Non Self Discrimination* (1982); Kennett, et al., *Monoclonal Antibodies and Hybridomas: A New Dimension in Biological Analyses* (1980); and Campbell, "Monoclonal Antibody Technology," in: *Laboratory Techniques in Biochemistry and Molecular Biology.*

The antibodies of the present invention may be used to detect the presence of CaR using any of a variety of immunoassays. For example, the antibodies may be used in radioimmunoassays or in immunometric assays, also known as "two-site" or "sandwich" assays (see Chard, "An Introduction to Radioimmune Assay and Related Techniques" in: *Laboratory Techniques in Biochemistry and Molecular Biology*, North Holland Publishing Co., N.Y. (1978)). Many variations of these types of assays may be employed for the detection of CaR.

The results obtained from the biopsy tissue should be compared with results obtained from tissue known to be normal. For example, the number of receptors present in prostate biopsy tissue would be compared to the number present in normal prostate tissue. Again, a statistically significant change in receptor number suggests that the biopsy tissue is cancerous.

Alternatively patients having an abnormal growth suspected of being cancerous may be directly administered a ligand that binds to CaR receptors with specificity. The ligand should be labeled with an agent that can be detected using an in vivo imaging technique and then administered to the patient. The amount of label that becomes localized within the abnormal growth may then be compared with surrounding tissue (or tissue otherwise known to be non-cancerous) to determine whether the growth is cancerous. For example, a radioactive isotope may be attached to a CaR-specific ligand and administered to a woman with a lump in her breast. The localization of radioactivity within the lump would suggest that it was cellularly dense and probably cancerous. In contrast, a lack of localization would suggest that the lump was more likely a cellularly sparse cyst. Other imaging techniques that may be used include computer assisted tomography, sonograms, nuclear imaging and magnetic resonance imaging.

All references cited herein are fully incorporated by reference. Having now fully described the invention, it will be understood by those of skill in the art that the invention may be performed within a wide and equivalent range of conditions, parameters and the like, without affecting the spirit or scope of the invention or any embodiment thereof.

What is claimed is:

1. A method of determining whether an abnormal growth on the breast, colon, lung, brain, ovary, skin, head or neck of a human patient is cancerous based upon the cellular density of said abnormal growth, comprising:
   a) administering to said patient a compound that binds with specificity to a calcium-sensing receptor (CaR) and that is labeled with an agent that allows said compound to be detected using in vivo imaging techniques;
   b) comparing the extent to which said detectably labeled compound of step a) becomes localized within said abnormal growth with the extent to which said detectably labeled compound of step a) becomes localized in tissues surrounding said abnormal growth;
   c) determining that said abnormal growth is cancerous if said detectably labeled compound is present in said abnormal growth at a higher density than in said surrounding tissue.

2. The method of claim 1, wherein said abnormal growth is a lump in the breast of a woman.

3. The method of claim 1, wherein said abnormal growth is present in the colon, lung or brain of said patient.

4. A method of determining whether an abnormal growth on the breast, colon, lung, brain, ovary, skin, head or neck of a patient is a cyst based upon the cellular density of said abnormal growth, comprising:
   a) administering to said patient a compound that binds with specificity to a calcium-sensing receptor (CaR) and that is labeled with an agent that allows said compound to be detected using in vivo imaging techniques;
   b) comparing the extent to which said detectably labeled compound of step a) becomes localized in said abnormal growth with the extent to which said detectably labeled compound of step a) becomes localized in tissue surrounding said abnormal growth; and
   c) determining that said abnormal growth is a cyst if said detectably labeled compound is present in said abnormal growth at a lower density than in said surrounding tissue.

5. The method of claim 4, wherein said abnormal growth is a lump in the breast of a woman.

6. The method of claim 4, wherein said abnormal growth is present in the colon, lung or brain of said patient.

* * * * *